(12) United States Patent
Oguma et al.

(10) Patent No.: US 9,329,105 B2
(45) Date of Patent: May 3, 2016

(54) SAMPLING METHOD AND SAMPLING DEVICE OF RECYCLED RAW MATERIAL, ANALYSIS SAMPLE OF RECYCLED RAW MATERIAL, AND EVALUATION METHOD OF RECYCLED RAW MATERIAL

(71) Applicant: MITSUBISHI MATERIALS CORPORATION, Tokyo (JP)

(72) Inventors: Nobuhiro Oguma, Tokyo (JP); Makoto Takagi, Kagawa-gun (JP); Eiji Wajima, Kagawa-gun (JP)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 0 days.

(21) Appl. No.: 14/400,726

(22) PCT Filed: Sep. 13, 2013

(86) PCT No.: PCT/JP2013/074845
§ 371 (c)(1),
(2) Date: Nov. 12, 2014

(87) PCT Pub. No.: WO2014/174699
PCT Pub. Date: Oct. 30, 2014

(65) Prior Publication Data
US 2015/0128731 A1   May 14, 2015

(30) Foreign Application Priority Data
Apr. 26, 2013 (JP) ................................. 2013-094734

(51) Int. Cl.
*G01N 1/22* (2006.01)
*G01N 1/04* (2006.01)
(Continued)

(52) U.S. Cl.
CPC .. *G01N 1/04* (2013.01); *B09B 3/00* (2013.01); *G01N 1/286* (2013.01); *G01N 1/38* (2013.01);
(Continued)

(58) Field of Classification Search
CPC ...................... G01N 1/405; G01N 2001/2217
USPC ...................................................... 73/863.21
See application file for complete search history.

(56) References Cited
U.S. PATENT DOCUMENTS
6,228,301 B1 * 5/2001 Taguchi et al. ............... 264/140

FOREIGN PATENT DOCUMENTS
JP    2003-010706 A    1/2003
JP    2003-106962 A    4/2003
(Continued)

OTHER PUBLICATIONS
International Search Report mailed Nov. 5, 2013, issued for PCT/JP2013/074845 and English translation thereof.
(Continued)

*Primary Examiner* — Hezron E Williams
*Assistant Examiner* — Rodney T Frank
(74) *Attorney, Agent, or Firm* — Locke Lord LLP

(57) ABSTRACT

Provided is a sampling method of recycled raw material, the method including: a process (S3) of primarily crushing recycled raw material; a process (S4 to S7) of separating primarily crushed raw material into three components, "scrap iron", "scrap aluminum", and "recycled raw material component other than scrap iron and scrap aluminum" and performing primary sample reductions of the three components; a process (S8 to S10) of secondarily crushing "the recycled raw material component other than scrap iron and scrap aluminum", which is subjected to the primary sample reduction, and performing a secondary sample reduction of "recycled raw material component other than scrap iron and scrap aluminum" which is secondarily crushed; and a mixing process (S12) of mixing "scrap iron" and "scrap aluminum" with "the recycled raw material component other than scrap iron and scrap aluminum" which is subjected to the secondary sample reduction.

20 Claims, 3 Drawing Sheets

(51) Int. Cl.
  *B09B 3/00* (2006.01)
  *G01N 1/40* (2006.01)
  *G01N 1/38* (2006.01)
  *G01N 5/00* (2006.01)
  *B09B 5/00* (2006.01)
  *G01N 1/28* (2006.01)

(52) U.S. Cl.
  CPC ............... *G01N 1/4077* (2013.01); *G01N 5/00* (2013.01); *B09B 5/00* (2013.01); *G01N 2001/2866* (2013.01)

(56) References Cited

FOREIGN PATENT DOCUMENTS

| JP | 2003-112156 A | 4/2003 |
| JP | 2003-126783 A | 5/2003 |
| JP | 2006-142129 A | 6/2006 |
| JP | 2008-249437 A | 10/2008 |
| JP | 2010-223905 A | 10/2010 |

OTHER PUBLICATIONS

Written Opinion of the International Preliminary Examining Authority mailed Jun. 3, 2014, issued for PCT/JP2013/074845 and English translation thereof.

Notice of Allowance mailed Apr. 7, 2015, issued for the Korean patent application No. 10-2014-7031962 and English translation thereof.

The extended European search report dated Dec. 18, 2015 issued for corresponding European Patent Application No. 13882888.4.

\* cited by examiner

SAMPLING METHOD AND SAMPLING DEVICE OF RECYCLED RAW MATERIAL, ANALYSIS SAMPLE OF RECYCLED RAW MATERIAL, AND EVALUATION METHOD OF RECYCLED RAW MATERIAL

TECHNICAL FIELD

The present invention relates to a sampling method and a sampling device of recycled raw material, an analysis sample of recycled raw material, and an evaluation method of recycled raw material, all of which are used for analysis and evaluation of recycled raw material containing a valuable metal other than iron (Fe) and aluminum (Al) such as gold (Au), silver (Ag), copper (Cu), platinum (Pt), or palladium (Pd).

Priority is claimed on Japanese Patent Application No. 2013-094734, filed Apr. 26, 2013, the content of which is incorporated herein by reference.

BACKGROUND ART

Electronic substrates which are used in electronic apparatuses, flexible substrates, IC chips, mobile phones, and the like contain gold, silver, copper, palladium, and the like. In addition, photographic films, cinematographic films, radiographic films, photographic papers, and the like contain silver. Techniques of reusing waste of these electronic substrates, IC chips, mobile phones, flexible substrates, films, photographic papers, and the like as recycled raw materials are proposed. For example, the above-described waste is burned in a rotary kiln furnace or the like to obtain combustion ash, this combustion ash is put into a copper smelting furnace or the like, and the above-described valuable metals are recovered in the process of copper smelting.

In recycled raw materials such as electronic substrates, IC chips, mobile phones, flexible substrates, films, and photographic papers, the transaction price thereof is determined based on the content of valuable metals included in the recycled raw materials. When an analysis sample is collected from recycled raw material by human labor, a portion having a high concentration of valuable metal or a portion having no valuable metal is separated and collected during the collection of the analysis sample, which may lead to an inaccurate evaluation of the recycled raw material. Accordingly, there may be a difference between evaluation of a delivery side of the recycled raw material and evaluation of a receiving side of the recycled raw material.

Therefore, in order to automatically obtain an analysis sample from recycled raw material, a sampling device and a sampling method are proposed. For example, PTL 1 discloses a sampling method of recycled raw material, the method including: a process of crushing recycled raw material; a primary mixing process of stirring and mixing the crushed material; a primary sample reduction process of performing a sample reduction of the stirred and mixed crushed material; a pulverization process of further pulverizing the crushed material which is subjected to the sample reduction; a secondary mixing process of stirring and mixing the pulverized material; and a secondary sample reduction process of performing a sample reduction of the stirred and mixed pulverized material, in which the pulverized material which is subjected to the secondary sample reduction process is set as an analysis sample.

In addition, PTL 2 discloses a method including: crushing recycled raw material with a crusher to obtain a primary crushed material; further crushing the primary crushed material with a crusher to obtain a secondarily crushed material; sieving the secondarily crushed material to separate a crushed material having a size of 30 mm or more; and crushing the crushed material again with a crusher to collect a crushed material having a size of 30 mm or less as a sample.

CITATION LIST

Patent Literature

[PTL 1] Japanese Unexamined Patent Application, First Publication No. 2010-223905

[PTL 2] Japanese Unexamined Patent Application, First Publication No. 2008-249437

SUMMARY OF INVENTION

Problem to be Solved by the Invention

Incidentally, in recycled raw material, for example, in an electronic substrate, each of scrap iron and scrap aluminum having high ductility such as an integrated circuit, a capacitor, and a heat sink is mixed in an amount of 1% to 25%. Therefore, with a common pulverizer, such as a double roll crusher or a rotary crusher, used for pulverizing recycled raw material, it is difficult to finely pulverize scrap iron and scrap aluminum having high ductility. Accordingly, in a state where scrap iron and scrap aluminum are mixed, it is also difficult to finely pulverize recycled raw material component other than scrap iron and scrap aluminum. On the other hand, since most of valuable metals other than scrap iron and scrap aluminum are present in the recycled raw material component other than scrap iron and scrap aluminum, it is preferable to finely pulverize the recycled raw material component other than scrap iron and scrap aluminum in order to form a sample. However, as described above, in recycled raw material, recycled raw material component other than scrap iron and scrap aluminum is mixed with scrap iron and scrap aluminum having high ductility. Therefore, use of the above-described common pulverizer alone is not sufficient for the requirement for refinement of an analysis sample. In addition, scrap iron and scrap aluminum are extremely localized in recycled raw material. Therefore, even if sampling is performed in a state where scrap iron and scrap aluminum are localized, an analysis sample is affected by segregation and there is a limit to uniformization of the analysis sample.

By using an impact type pulverizer such as a turbo mill or a jet mill, recycled raw material can be finely pulverized even in a state where scrap iron and scrap aluminum are mixed. However, the impact type pulverizer is for processing an extremely small amount of recycled raw material and is not suitable for automatically obtaining an analysis sample from recycled raw material.

In this way, in the related art, there is a limit when recycled raw material component other than scrap iron and scrap aluminum is finely pulverized using the above-described common pulverizer, and an analysis sample is easily affected by the localization of scrap iron and scrap aluminum. Therefore, there is a limit to uniformization of the analysis sample. It is difficult to solve these problems even with the sampling methods disclosed in PTLs 1 and 2.

According to the present invention, there are provided a sampling method and a sampling device of recycled raw material in which a uniform analysis sample can be collected and an accurate evaluation can be performed; and an analysis sample.

Means for Solving the Problem

According to a first aspect of the present invention, there is provided a sampling method of recycled raw material, the method including: a process of primarily crushing recycled raw material; a process of separating primarily crushed raw material into three components, "scrap iron", "scrap aluminum", and "recycled raw material component other than scrap iron and scrap aluminum"; a process of performing a primary sample reduction of "the recycled raw material component other than scrap iron and scrap aluminum" which is separated at least after the primary crushing process; and a process of secondarily crushing "the recycled raw material component other than scrap iron and scrap aluminum", which is subjected to the primary sample reduction, into a size less than that in the primary crushing process and performing a secondary sample reduction of "the recycled raw material component other than scrap iron and scrap aluminum" which is secondarily crushed, and a process of obtaining a weight ratio of the three components, "scrap iron", "scrap aluminum", and "recycled raw material component other than scrap iron and scrap aluminum" which are primarily crushed, wherein the three components, "scrap iron", "scrap aluminum", and "the recycled raw material component other than scrap iron and scrap aluminum" which is subjected to the secondary sample reduction are set as analysis samples.

According to this configuration, the sample in which "the recycled raw material component other than scrap iron and scrap aluminum" is finely pulverized without being affected by "scrap iron" and "scrap aluminum" can be collected, the sample of "the recycled raw material component other than scrap iron and scrap aluminum" can be obtained without being affected by the localization of "scrap iron" and "scrap aluminum", and the uniformity of each of the three components can be improved.

In addition, according to a second aspect of the present invention, there is provided a sampling method of recycled raw material, the method including: a process of primarily crushing recycled raw material; a process of separating primarily crushed raw material into three components, "scrap iron", "scrap aluminum", and "recycled raw material component other than scrap iron and scrap aluminum"; a process of performing a primary sample reduction of "the recycled raw material component other than scrap iron and scrap aluminum" which is separated at least after the primary crushing process; a process of secondarily crushing "the recycled raw material component other than scrap iron and scrap aluminum", which is subjected to the primary sample reduction, into a size less than that in the primary crushing process and performing a secondary sample reduction of "the recycled raw material component other than scrap iron and scrap aluminum" which is secondarily crushed; a process of obtaining a weight ratio of the three components, "scrap iron", "scrap aluminum", and "the recycled raw material component other than scrap iron and scrap aluminum" which are primarily crushed; and a mixing process of mixing "scrap iron", "scrap aluminum" and "the recycled raw material component other than scrap iron and scrap aluminum" which is subjected to the secondary sample reduction at a mixing ratio corresponding to the weight ratio obtained in the previous process, wherein a mixture obtained in the mixing process is set as an analysis sample.

According to this configuration, "the recycled raw material component other than scrap iron and scrap aluminum" can be finely pulverized without being affected by "scrap iron" and "scrap aluminum". In addition, a uniform evaluation sample can be collected without being affected by the localization of "scrap iron" and "scrap aluminum".

In addition, according to a third aspect of the present invention, there is provided a sampling method of recycled raw material, the method including: a process of primarily crushing recycled raw material; a process of separating primarily crushed raw material into three components, "scrap iron", "scrap aluminum", and "recycled raw material component other than scrap iron and scrap aluminum" from the primarily crushed raw material and performing primary sample reductions of the three components; a process of secondarily crushing "the recycled raw material component other than scrap iron and scrap aluminum", which is subjected to the primary sample reduction, into a size less than that in the primary crushing process and performing a secondary sample reduction of "the recycled raw material component other than scrap iron and scrap aluminum" which is secondarily crushed; a process of obtaining a weight ratio of the three components, "scrap iron", "scrap aluminum", and "the recycled raw material component other than scrap iron and scrap aluminum" which are primarily crushed; and a mixing process of mixing "scrap iron", "scrap aluminum" which are subjected to the primary sample reduction, and "the recycled raw material component other than scrap iron and scrap aluminum" which is subjected to the secondary sample reduction at a mixing ratio corresponding to the weight ratio obtained in the previous process, wherein a mixture obtained in the mixing process is set as an analysis sample.

According to this configuration, uniformity can be further improved.

Here, in the process of obtaining a weight ratio of the three components, "scrap iron", "scrap aluminum", and "the recycled raw material component other than scrap iron and scrap aluminum" which are primarily crushed, it is preferable that the weight of each of the three components, "scrap iron", "scrap aluminum", and "the recycled raw material component other than scrap iron and scrap aluminum" which are primarily crushed be measured to obtain the weight ratio.

According to this configuration, the weight of each of the three components, "scrap iron", "scrap aluminum", and "the recycled raw material component other than scrap iron and scrap aluminum" which are primarily crushed is measured to obtain the weight ratio. Therefore, the weight ratio can be simply calculated.

In addition, as another configuration, it is preferable that the process of obtaining a weight ratio of the three components, "scrap iron", "scrap aluminum", and "recycled raw material component other than scrap iron and scrap aluminum" which are primarily crushed include a process of measuring the total weight of the recycled raw material before or after the primary crushing process, a process of measuring the weight of each of "scrap iron" and "scrap aluminum" which are separated after the primary crushing process, and a process of obtaining a weight ratio of the three components, "scrap iron", "scrap aluminum" and "the recycled raw material component other than scrap iron and scrap aluminum" based on a calculation result of the weight of "the recycled raw material component other than scrap iron and scrap aluminum", which is obtained by subtracting the weight of "scrap iron" and the weight of "scrap aluminum" from the total weight of the recycled raw material, and the respective weights of "scrap iron" and "scrap aluminum".

According to this configuration, the measurement of "the recycled raw material component other than scrap iron and scrap aluminum" which is primarily crushed can be omitted.

In addition, in the primary crushing process, it is preferable that the recycled raw material be crushed into a size of 20 mm or less.

According to this configuration, a load on the secondary crushing process which is the subsequent process can be reduced. In addition, due to the refinement of "scrap iron" and "scrap aluminum", the uniformity of an analysis sample can be improved.

"The recycled raw material is crushed into a size of 20 mm or less" described herein implies that the recycled raw material is crushed into a size so as to pass through a sieve having a mesh size of 20 mm. In addition, the same shall be applied to a case where the recycled raw material is crushed into a size other than 20 mm.

In addition, in the secondary crushing process, it is preferable that "the recycled raw material component other than scrap iron and scrap aluminum" be crushed into a size of 5 mm or less.

According to this configuration, the uniformity of an analysis sample can be further improved.

According to the present invention, there is provided a sampling device including: a primary crusher that primarily crushes recycled raw material; an Fe separator that separates "scrap iron" from the primarily crushed raw material; a Al separator that separates "scrap aluminum" from the primarily crushed raw material; recycled raw material-component-other-than-scrap iron-and-scrap aluminum primary sample reduction machine that performs a sample reduction of "recycled raw material component other than scrap iron and scrap aluminum" from which "scrap iron" and "scrap aluminum" are removed by the Fe separator and the Al separator; a secondary crusher that secondarily crushes "the recycled raw material component other than scrap iron and scrap aluminum", which is subjected to the sample reduction by the recycled-raw-material-component-other-than-scrap iron-and-scrap aluminum primary sample reduction machine, into a size less than that obtained by the primary crusher; and a secondary sample reduction machine that performs a secondary sample reduction of "the recycled raw material component other than scrap iron and scrap aluminum" which is secondarily crushed by the secondary crusher; a measuring device that measures the weights of the three components, "scrap iron", "scrap aluminum", and "recycled raw material component other than scrap iron and scrap aluminum" which are separated from the primarily crushed raw material; and a mixing device that mixes "scrap iron", "scrap aluminum", and "recycled raw material component other than scrap iron and scrap aluminum" with each other at a predetermined mixing ratio set according to a measurement result of the measuring device.

According to this configuration, the first sampling method according to the present invention can be realized.

According to the present invention, there is provided a sampling device including: a primary crusher that primarily crushes recycled raw material; an Fe separator that separates "scrap iron" from the primarily crushed raw material; an Al separator that separates "scrap aluminum" from the primarily crushed raw material; recycled raw material-component-other-than-scrap-iron-and-scrap-aluminum primary sample reduction machine that performs a sample reduction of "recycled raw material component other than scrap-iron and scrap aluminum" from which "scrap iron" and "scrap aluminum" are removed by the Fe separator and the Al separator; a secondary crusher that secondarily crushes "the recycled raw material component other than scrap iron and scrap aluminum", which is subjected to the sample reduction by the recycled-raw-material-component-other-than- scrap-iron-and- scrap-aluminum primary sample reduction machine, into a size less than that obtained by the primary crusher; a secondary sample reduction machine that performs a secondary sample reduction of "the recycled raw material component other than scrap iron and scrap aluminum" which is secondarily crushed by the secondary crusher; a measuring device that measures the total weight of the recycled raw material and the weight of each of two components including "scrap iron" and "scrap aluminum" which are separated from the primarily crushed raw material; and a mixing device that mixes "scrap iron", "scrap aluminum", and "the recycled raw material component other than scrap iron and scrap aluminum" with each other at a predetermined mixing ratio set according to a measurement result of the measuring device.

In addition, it is preferable that the sampling device further include a scrap iron primary sample reduction machine that performs a primary sample reduction of "scrap iron" which is separated by the Fe separator; and a scrap aluminum primary sample reduction machine that performs a primary sample reduction of "scrap aluminum" which is separated by the Al separator.

According to this configuration, the third sampling method according to the present invention can be realized.

In addition, it is preferable that the Fe separator be a magnetic separator and that the Al separator be an eddy current separator.

According to this configuration, with electrical means, "scrap iron" and "scrap aluminum" can be separated from the primarily crushed raw material.

In addition, according to an aspect of the present invention, there is provided an analysis sample of recycled raw material which is sampled using the above-described sampling method.

According to this analysis sample, recycled raw material can be accurately evaluated.

In addition, according to an aspect of the present invention, there is provided an evaluation method of recycled raw material, the method including: a process of mixing "scrap iron", "scrap aluminum", and "recycled raw material component other than scrap iron and scrap aluminum", which are obtained using the sampling method of recycled raw material, with each other to obtain an analysis sample; and a process of performing an elementary analysis of the analysis sample to measure the content of valuable metals in a certain number of samples.

According to this configuration, the content of valuable metals in recycled raw material can be accurately and stably evaluated.

Effects of the Invention

In the sampling method according to claim 1, "recycled raw material component other than scrap iron and scrap aluminum", which is a residual material obtained after removing "scrap iron" and "scrap aluminum" from the primarily crushed recycled raw material, is subjected to the primary sample reduction, is secondarily crushed into a smaller size, and then is subjected to the secondary sample reduction. As a result, the sample in which "the recycled raw material component other than scrap iron and scrap aluminum" is finely pulverized without being affected by "scrap iron" and "scrap aluminum" having high ductility can be collected. In addition, "scrap iron" and "scrap aluminum" are separated in advance from the recycled raw material aside from "the recycled raw material component other than scrap iron and scrap aluminum" which is the residual material. As a result, the sample of "the recycled raw material component other than scrap iron and scrap aluminum" can be obtained without being affected by the localization of "scrap iron" and "scrap aluminum". Accordingly, the uniformity of each of the three components can be improved, and an accurate evaluation can be performed.

In the sampling method according to claim 2, "recycled raw material component other than scrap iron and scrap aluminum", which is a residual material obtained after removing "scrap iron" and "scrap aluminum" from the primarily crushed recycled raw material, is subjected to the primary sample reduction, is secondarily crushed into a smaller size, and then is subjected to the secondary sample reduction. As a result, "recycled raw material component other than scrap iron and scrap aluminum" can be finely pulverized without being affected by "scrap iron" and "scrap aluminum" having high ductility. In addition, according to the weight ratio of the three components, "scrap iron", "scrap aluminum", and "the recycled raw material component other than scrap iron and scrap aluminum" in the recycled raw material, "scrap iron" and "scrap aluminum" which are separated in advance are mixed with "recycled raw material component other than scrap iron and scrap aluminum" which is subjected to the secondary sample reduction. As a result, a uniform evaluation sample can be collected without being affected by the localization of "scrap iron" and "scrap aluminum", and an accurate evaluation can be performed.

In the sampling method according to claim 3, the three components, "scrap iron", "scrap aluminum", and "the recycled raw material component other than scrap iron and scrap aluminum" are separated from the primarily crushed raw material, and the primary sample reductions of the three components are performed. As a result, uniformity can be further improved.

In the sampling method according to claim 4, the weight of each of the three components, "scrap iron", "scrap aluminum", and "the recycled raw material component other than scrap iron and scrap aluminum" which are primarily crushed is measured to obtain the weight ratio. Therefore, the weight ratio can be simply calculated.

In the sampling method according to claim 5, the weight ratio of the three components, "scrap iron", "scrap aluminum", and "the recycled raw material component other than scrap iron and scrap aluminum" is obtained based on the total weight of the recycled raw material and the respective weights of "scrap iron" and "scrap aluminum". As a result, the measurement of "recycled raw material component other than scrap iron and scrap aluminum" which is primarily crushed can be omitted.

In the sampling method according to claim 6, in the primary crushing process, the recycled raw material is crushed into a size of 20 mm or less. As a result, a load on the secondary crushing process which is the subsequent process can be reduced. In addition, due to the refinement of "scrap iron" and "scrap aluminum", the uniformity of an analysis sample can be improved.

In the sampling method according to claim 7, in the secondary crushing process, "the recycled raw material component other than scrap iron and scrap aluminum" is crushed into a size of 5 mm or less. As a result, due to the refinement of "the recycled raw material component other than scrap iron and scrap aluminum" containing a large amount of valuable metals, the uniformity of an analysis sample can be improved.

With the sampling device according to claim 8, the sampling method according to claim 1 can be realized.

With the sampling device according to claim 9, the sampling method according to claim 2 can be realized.

With the sampling device according to claim 10, the sampling method according to claim 3 can be realized.

In the sampling device according to claim 11, the magnetic separator is used as the Fe separator, and the eddy current separator is used as the Al separator. As a result, with electrical means, "scrap iron" and "scrap aluminum" can be separated from the primarily crushed raw material.

With the analysis sample according to claim 12, recycled raw material can be accurately evaluated.

With the evaluation method according to claim 13, the content of valuable metals in recycled raw material can be accurately evaluated.

DESCRIPTION OF EMBODIMENTS

Hereinafter, an embodiment of the present invention will be described with reference to the accompanying drawings.

Figure 1:
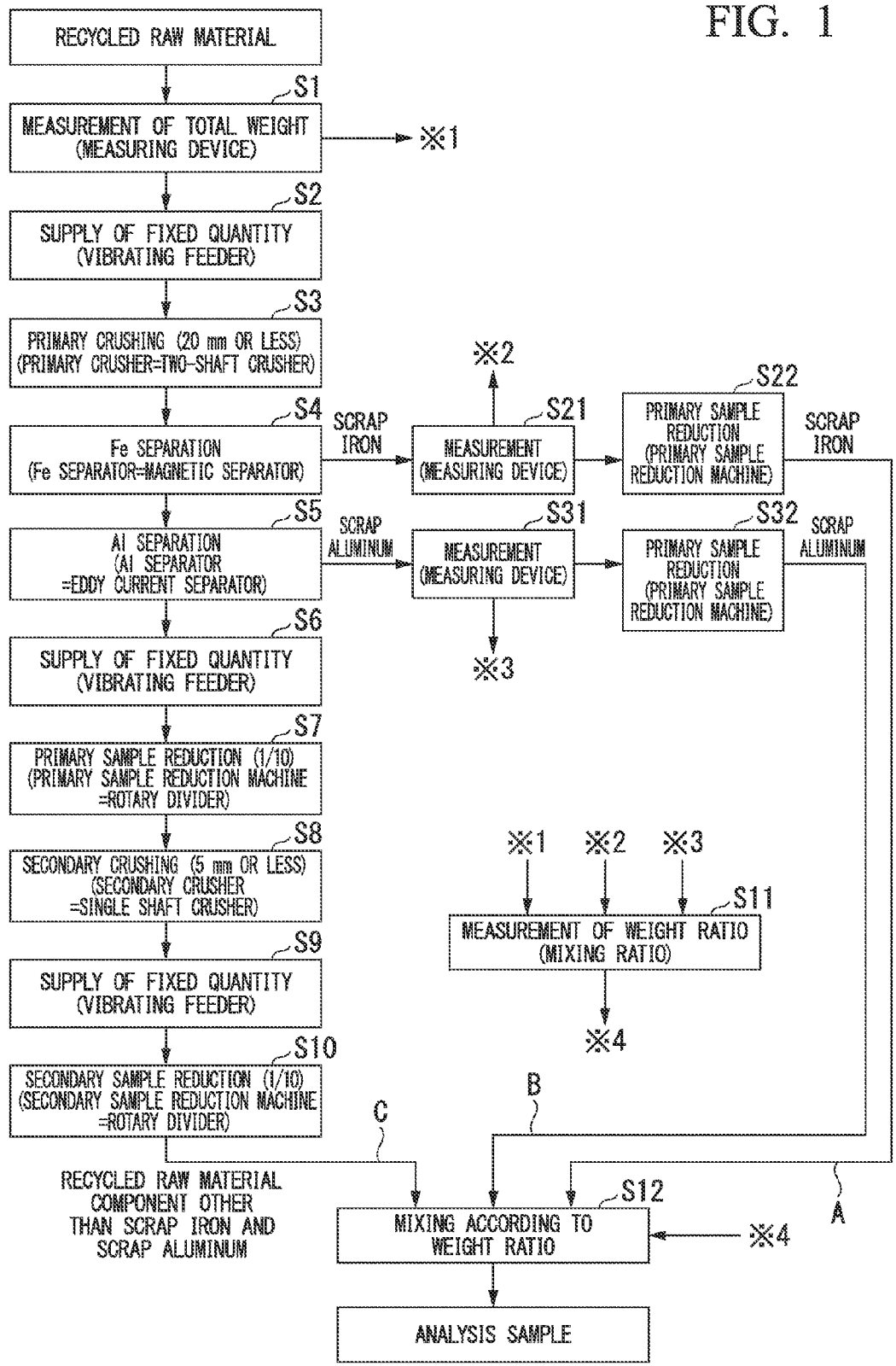
FIG. 1 is a diagram illustrating a sampling method and a sampling device according to an embodiment of the present invention.

FIG. 1 is a diagram illustrating a sampling method and a sampling device according to the embodiment.

Here, examples of recycled raw material processed by the sampling method and the sampling device according to the embodiment include printed substrates, flexible substrates, IC chips, mobile phones, films, and photographic papers. These recycled raw materials contain valuable metals such as gold, silver, and copper, and the price of the recycled raw materials is determined based on the content of the valuable metals.

The sampling method and the sampling device will be described using FIG. 1. In the sampling method according to the embodiment, first, the total weight of the recycled raw material is measured using a measuring device (S1).

Next, while supplying a fixed quantity of the recycled raw material by a quantitative supply device (for example a vibrating feeder) (S2), the recycled raw material is primarily crushed into a size of 20 mm or less by a primary crusher (for example, a two-shaft crusher) for coarse crushing (S3).

After the primary crushing process, "scrap iron" is separated from the recycled raw material by an Fe separator (for example, a magnetic separator) (S4). The weight of the separated "scrap iron" is measured by the measuring device (S21), and a primary sample reduction thereof is performed by a primary sample reduction machine (S22).

In addition, "scrap aluminum" is separated, by an Al separator (for example, an eddy current separator), from the recycled raw material from which "scrap iron" is removed (S5). The weight of the separated "scrap aluminum" is measured by the measuring device (S31), and a primary sample reduction thereof is performed by a primary sample reduction machine (S32).

Next, while supplying a fixed quantity of "the recycled raw material component other than scrap iron and scrap aluminum" from which "scrap iron" and "scrap aluminum" are removed by a quantitative supply device (for example, a vibrating feeder) (S6), a primary sample reduction thereof is performed by a primary sample reduction machine (for example, a rotary divider) such that the volume thereof is reduced to 1/10 (S7). "The recycled raw material component other than scrap iron and scrap aluminum" which is subjected to the primary sample reduction is secondarily crushed into a size of 5 mm or less, which is smaller than that obtained by the primary crusher, by a secondary crusher (for example, a single shaft crusher) (S8). Next, while supplying a fixed quantity of "the recycled raw material component other than scrap iron and scrap aluminum", which is secondarily crushed, by a quantitative supply device (for example, a vibrating feeder) (S9), a secondary sample reduction thereof is performed by a secondary sample reduction machine (for example, a rotary divider) such that the volume thereof is reduced to 1/10 (S10).

Meanwhile, the total weight of the recycled raw material is measured before the primary crushing process, and the weight of each of "scrap iron" and "scrap aluminum" which are separated is measured after the primary crushing process. Therefore, a weight ratio of the three components, "scrap iron", "scrap aluminum" and "the recycled raw material component other than scrap iron and scrap aluminum" is obtained based on a calculation result of the weight of "the recycled raw material component other than scrap iron and scrap aluminum", which is obtained by subtracting the weight of "scrap iron" and the weight of "scrap aluminum" from the total weight of the recycled raw material, and the respective weights of "scrap iron" and "scrap aluminum" (S11). Next, "scrap iron" A, "scrap aluminum" B which are subjected to the primary sample reduction, and "the recycled raw material component other than scrap iron and scrap aluminum" C which is secondarily crushed and subjected to the secondary sample reduction are mixed at a mixing ratio corresponding to the calculated weight ratio, and a mixture thereof is set as an analysis sample (S12).

Figure 2:
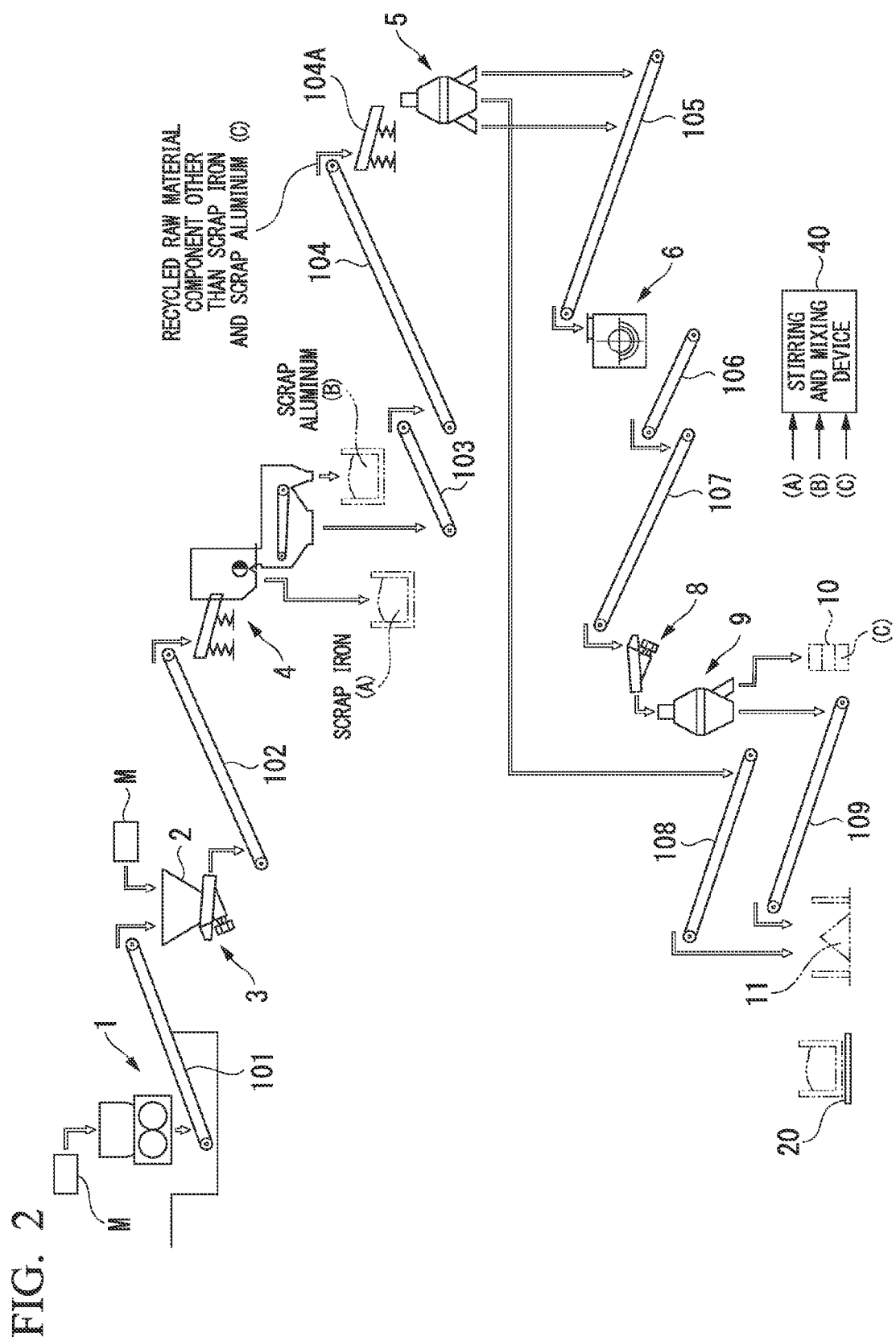
FIG. 2 is a system diagram illustrating a specific configuration of the sampling device according to the embodiment.
Figure 3:
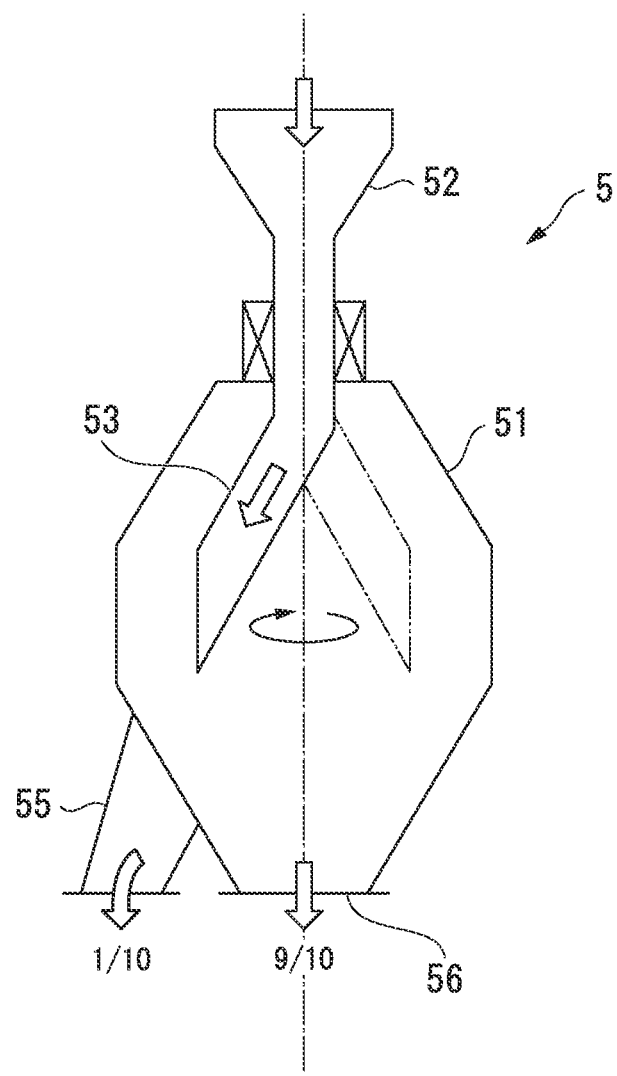
FIG. 3 is a diagram illustrating a rotary divider used in the sampling device according to the embodiment.

FIG. 2 is a system diagram illustrating a specific configuration of the sampling device according to the embodiment, and FIG. 3 is a diagram illustrating a rotary divider used in the sampling device.

The sampling device illustrated in FIG. 2 includes a primary crusher 1 that primarily crushes recycled raw material M which is put thereinto. A two-shaft crusher which is used as the primary crusher 1 crushes the raw material into a size of 20 mm or less. The primarily crushed raw material is transported to a receiving hopper 2 by a transport conveyor 101. Components of the recycled raw material M which do not need to be primarily crushed are also put into the receiving hopper 2. A vibrating feeder (quantitative supply device) 3 is provided in an outlet of the receiving hopper 2 such that the vibrating feeder 3 supplies a fixed quantity of the raw material to a transport conveyor 102. The raw material supplied to the transport conveyor 102 is put into an aluminum separator (Al separator) 4 equipped with a drum magnetic separator (Fe separator) such that "scrap iron" A and "scrap aluminum" B are separated from the recycled raw material there.

"The recycled raw material component other than scrap iron and scrap aluminum" C from which "scrap iron" A and "scrap aluminum" B are removed by passing through the aluminum separator 4 equipped with the drum magnetic separator passes through transport conveyors 103 and 104 and a vibrating feeder 104A and then is put into a rotary divider 5 which is a primary sample reduction machine. In the rotary divider 5, as illustrated in FIG. 3, a rotary chute 53 having a receiving port 52 at an upper end thereof is provided inside a container body 51. Therefore, by rotating the rotary chute 53 while putting the raw material thereinto, a part of the put raw material is subjected to a sample reduction and discharged from a divider outlet 55, and the other part thereof is discharged from an unnecessary part outlet 56.

When the primary sample reductions of "scrap iron" A and "scrap aluminum" B, which are primarily crushed and respectively separated, are performed in step S22 and step S32, this type of rotary divider 5 is used.

"The recycled raw material component other than scrap iron and scrap aluminum" C which is subjected to the primary sample reduction in the rotary divider 5 is supplied to a secondary crusher 6 through a transport conveyor 105. A single shaft crusher which is used as the secondary crusher 6 crushes "recycled raw material component other than scrap iron and scrap aluminum" C into a size of 5 mm or less. The crushed raw material is transported to a vibrating feeder (quantitative supply device) 8 through transport conveyors 106 and 107, and a fixed quantity thereof is supplied and put into a rotary divider 9 which is a secondary sample reduction machine. "The recycled raw material component other than scrap iron and scrap aluminum" C whose volume is reduced to 1/10 by the rotary divider 9 is stored in a drum can 10.

In addition, this sampling device includes a measuring device 20. This measuring device 20 is used when the total weight of the recycled raw material is measured before the primary crushing process and when the weight of each of "scrap iron" and "scrap aluminum" is measured after the primary crushing process. When the total weight of the recycled raw material, the weight of "scrap iron" A, and the weight of "scrap aluminum" B are obtained, the weight of "the recycled raw material component other than scrap iron and scrap aluminum" C can be calculated by subtracting the weight of "scrap iron" A and the weight of "scrap aluminum" B from the total weight of the recycled raw material.

Accordingly, a weight ratio of three components, "scrap iron", "scrap aluminum", and "the recycled raw material component other than scrap iron and scrap aluminum" can be calculated based on the above calculation result and the respective weights of "scrap iron" and "scrap aluminum" which are previously measured. Next, "scrap iron" A and "scrap aluminum" B which are subjected to the primary sample reduction and "recycled raw material component other than scrap iron and scrap aluminum" C which is secondarily crushed and subjected to the secondary sample reduction are put into a stirring and mixing device 40, followed by mixing at a mixing ratio corresponding to the calculated weight ratio. As a result, a mixture can be obtained as an analysis sample.

In this sampling device, a component of the raw material which is unnecessary in the rotary divider 5 and 9 is transported to an abandoned mine yard 11 through discharge conveyors 108 and 109.

In the above-described sampling method and sampling device according to the above-described embodiment, "the recycled raw material component other than scrap iron and scrap aluminum", which is a residual material obtained after removing "scrap iron" and "scrap aluminum" from the primarily crushed recycled raw material, is subjected to the primary sample reduction, is secondarily crushed into a smaller size, and then is subjected to the secondary sample reduction. Therefore, even if a common crusher such as a single shaft shearing crusher used for pulverizing recycled raw material is used instead of a special crusher such as an impact type pulverizer, "the recycled raw material component other than scrap iron and scrap aluminum" can be finely pulverized into a size of 5 mm or less without being affected by "scrap iron" and "scrap aluminum" having highductility.

In addition, according to the weight ratio of the three components, "scrap iron", "scrap aluminum", and "the recycled raw material component other than scrap iron and scrap aluminum" in the recycled raw material, "scrap iron" A and "scrap aluminum" B which are separated in advance are mixed with "the recycled raw material component other than scrap iron and scrap aluminum" C which is subjected to the secondary sample reduction. As a result, a uniform analysis sample can be collected without being affected by the localization of "scrap iron" and "scrap aluminum", and an accurate evaluation of the recycled raw material can be performed.

In addition, the three components, "scrap iron", "scrap aluminum", and "the recycled raw material component other than scrap iron and scrap aluminum" are separated from the primarily crushed raw material, and the primary sample reductions of the three components are performed. As a result, uniformity can be further improved.

In addition, in the embodiment, the weight ratio of the three components, "scrap iron", "scrap aluminum", and "the recycled raw material component other than scrap iron and scrap aluminum" is obtained based on the total weight of the recycled raw material and the respective weights of "scrap iron" and "scrap aluminum" which are measured by the measuring device. As a result, the measurement of "recycled raw material component other than scrap iron and scrap aluminum" which is primarily crushed can be omitted.

In addition, in the embodiment, in the primary crushing process, the recycled raw material is crushed into a size of 20 mm or less. As a result, a load on the secondary crushing process which is the subsequent process can be reduced. In addition, due to the refinement of "scrap iron" and "scrap aluminum", the uniformity of an analysis sample can be improved. In addition, in the secondary crushing process, "the recycled raw material component other than scrap iron and scrap aluminum" is crushed into a size of 5 mm or less. As a result, due to the refinement of "the recycled raw material component other than scrap iron and scrap aluminum" containing a large amount of valuable metals, the uniformity of an analysis sample can be improved. In addition, the magnetic separator is used as the Fe separator, and the eddy current separator is used as the Al separator. As a result, with electrical means, "scrap iron" and "scrap aluminum" can be automatically separated from the primarily crushed raw material.

The present invention is not limited to the above-described embodiment described with reference to the drawings, and various modification examples can be adopted within the technical scope of the present invention.

For example, in the process of obtaining a weight ratio of the three components, "scrap iron", "scrap aluminum", and "the recycled raw material component other than scrap iron and scrap aluminum" which are primarily crushed, the weight of each of the three components, "scrap iron", "scrap aluminum", and "the recycled raw material component other than scrap iron and scrap aluminum" which are primarily crushed may be measured to obtain the weight ratio.

In addition, the primary sample reductions of "scrap iron" and "scrap aluminum" are not necessarily performed.

In addition, in the above-described embodiment, "scrap iron", "scrap aluminum", and "the recycled raw material component other than scrap iron and scrap aluminum" which is subjected to the secondary sample reduction are mixed at the weight ratio to obtain an analysis sample. However, each of the three components, "scrap iron" A, "scrap aluminum" B, "the recycled raw material component other than scrap iron and scrap aluminum" C which is subjected to the secondary sample reduction may be adopted as an individual analysis sample.

Even in this case, "the recycled raw material component other than scrap iron and scrap aluminum", which is a residual material obtained after removing "scrap iron" and "scrap aluminum" from the primarily crushed recycled raw material, is subjected to the primary sample reduction, is secondarily crushed into a smaller size, and then is subjected to the secondary sample reduction. As a result, the sample in which "the recycled raw material component other than scrap iron and scrap aluminum" is finely pulverized without being affected by "scrap iron" and "scrap aluminum" having high ductility can be collected. In addition, "scrap iron" and "scrap aluminum" are separated in advance from the recycled raw material aside from "the recycled raw material component other than scrap iron and scrap aluminum" which is the residual material. As a result, the sample of "the recycled raw material component other than scrap iron and scrap aluminum" can be obtained without being affected by the localization of "scrap iron" and "scrap aluminum". Accordingly, the uniformity of each of the three components can be improved, and an accurate evaluation can be performed.

EXAMPLES

Next, the results of a verification test which was performed to verify the effects of the present invention will be described.

In this verification test, 5 types of electronic substrates (Samples 1 to 5) having a relatively high grade of valuable metal were prepared as recycled raw materials. In these electronic substrates, IC chips, integrated circuits, capacitors, heat sinks, or the like are mounted on a printed substrate.

In comparative examples, each of the recycled raw materials was crushed into a size of 20 mm or less by a primary crusher and was subjected to a sample reduction by a primary sample reduction machine such that the volume thereof was reduced to 10%. At this time, a magnetic separator and an eddy current separator were not used (scrap iron and scrap aluminum were not separated). The recycled raw material was crushed into a size of 10 mm or less which was a final crushing size by a secondary crusher, and a sample reduction thereof was performed by a secondary sample reduction machine. As a result, multiple (three) analysis samples were collected and were analyzed and evaluated for valuable metals (Au, Ag, Cu, Pd).

In addition, in examples according to the present invention, samples for analysis and evaluation were collected using the sampling device of recycled raw material according to the embodiment and were analyzed and evaluated for valuable metals. That is, the total weight of 0.5 ton to 1 ton each of the same recycled raw materials as those used in the comparative examples was measured, and the recycled raw material was crushed into a size of 20 mm or less using a two-shaft shearing crusher (primary crusher). Next, scrap iron was removed from the recycled raw material using a drum magnetic separator having a magnetic flux density of 0.1 T (tesla). Further, scrap aluminum was removed from the recycled raw material other than scrap iron using a magnetic rotor eddy current separator having a magnetic flux density of 0.2 T (tesla). Next, recycled raw material component other than scrap iron and scrap aluminum was crushed into a size of 5 mm or less using a single shaft shearing crusher (secondary crusher), and a sample reduction thereof was performed using a secondary sample reduction machine. The above-described components were mixed at a mixing ratio calculated from a weight ratio of the original raw material, scrap iron, and scrap aluminum. As a result, multiple (three) analysis samples were collected and were analyzed and evaluated for valuable metals.

In the verification test using the examples according to the present invention, each of Samples 1 to 5 is separated into three components, "scrap iron", "scrap aluminum", and "the recycled raw material component other than scrap iron and scrap aluminum". The measurement results of the three components are shown in Table 1. Samples 1 to 5 contain each of "scrap iron" and "scrap aluminum" in an amount of 8 wt % to 20 wt %.

TABLE 1

|  | Raw Material Recycled Raw Material kg | Weight of Each of Three Components Separated From Raw Material | | |
|---|---|---|---|---|
|  |  | scrap iron kg | scrap aluminum kg | Recycled Raw Component Other than scrap iron and scrap aluminum kg |
| Sample 1 | 624.7 | 115.4 | 51.4 | 457.9 |
| Sample 2 | 518.8 | 90.8 | 41.5 | 386.5 |
| Sample 3 | 1,251.4 | 251.5 | 82.0 | 917.9 |
| Sample 4 | 1,203.8 | 174.6 | 115.3 | 914.0 |
| Sample 5 | 1,129.6 | 126.5 | 101.3 | 901.8 |

After the three components were mixed with each other at a mixing ratio (weight of scrap iron:weight of scrap aluminum:weight of recycled raw material component other than scrap iron and scrap aluminum) calculated from the weights to form an analysis sample, the analysis sample was analyzed and evaluated for valuable metals (Au, Ag, Cu, Pd). Specifically, Au, Ag, and PD were measured by plasma emission spectrometry, and Cu was measured by titrimetry. Analysis values of the recycled raw material (the contents (mass %) of Au, Ag, Cu, and Pd in the recycled raw material) were calculated based on the analysis and evaluation results and the weight ratio. The results of values of coefficient of variation (CV) of the analysis values of the recycled raw materials (Samples 1 to 5) of the examples and the comparative examples are shown in Table 2 below.

Value (%) of Coefficient of Variation(CV)=(Standard Deviation $n$/Average Analysis Value $n$)×100

The standard deviation and the average analysis value were calculated from the three analysis samples which were collected from each of Samples 1 to 5 as described above.

TABLE 2

|  | Sample Name | Value of Coefficient of Variation (CV) | | | |
|---|---|---|---|---|---|
|  |  | Au | Ag | Cu | Pd |
| Examples | Sample 1 | 1.7 | 1.9 | 1.9 | 1.6 |
|  | Sample 2 | 0.9 | 0.9 | 1.6 | 1.8 |
|  | Sample 3 | 1.7 | 1.6 | 1.6 | 1.8 |
|  | Sample 4 | 1.6 | 1.3 | 1.5 | 1.4 |
|  | Sample 5 | 0.7 | 1.4 | 1.2 | 1.5 |
| Comparative Examples | Sample 1 | 5.2 | 5.0 | 5.1 | 6.6 |
|  | Sample 2 | 6.1 | 5.1 | 3.8 | 7.9 |
|  | Sample 3 | 6.8 | 5.9 | 2.9 | 4.9 |
|  | Sample 4 | 5.3 | 5.1 | 2.4 | 5.7 |
|  | Sample 5 | 4.1 | 3.0 | 2.7 | 7.3 |

Value (%) of Coefficient of Variation (CV) = (Standard Deviation n/Average Analysis Value n) × 100

It was verified from Table 2 that all coefficients of variation of the examples according to the present invention were lower than those of the comparative examples, a variation thereof was small, and the analysis values were stable.

INDUSTRIAL APPLICABILITY

According to the present invention, "the recycled raw material component other than scrap iron and scrap aluminum", which is a residual material obtained after removing "scrap iron" and "scrap aluminum" from the primarily crushed recycled raw material, is subjected to the primary sample reduction, is secondarily crushed into a smaller size, and then is subjected to the secondary sample reduction. As a result, the sample in which "the recycled raw material component other than scrap iron and scrap aluminum" is finely pulverized without being affected by "scrap iron" and "scrap aluminum" having high ductility can be collected. In addition, "scrap iron" and "scrap aluminum" are separated in advance from the recycled raw material aside from "recycled raw material component other than scrap iron and scrap aluminum" which is the residual material. As a result, the sample of "the recycled raw material component other than scrap iron and scrap aluminum" can be obtained without being affected by the localization of "scrap iron" and "scrap aluminum". Accordingly, the uniformity of each of the three components can be improved, and an accurate evaluation can be performed. Accordingly, the present invention is industrially applicable.

REFERENCE SIGNS LIST

M: RECYCLED RAW MATERIAL
A: "scrap iron"
B: "scrap aluminum"
C: "RECYCLED RAW MATERIAL COMPONENT OTHER THAN scrap iron AND scrap aluminum"
1: PRIMARY CRUSHER
4: ALUMINUM SEPARATOR EQUIPPED WITH DRUM MAGNETIC SEPARATOR (Fe SEPARATOR, Al SEPARATOR)
5: ROTARY DIVIDER (RECYCLED-RAW-MATERIAL-COMPONENT-OTHER-THAN-scrap iron-AND-scrap aluminum PRIMARY SAMPLE REDUCTION MACHINE)
6: SECONDARY CRUSHER
9: ROTARY DIVIDER (SECONDARY SAMPLE REDUCTION MACHINE)
20: MEASURING DEVICE
40: STIRRING AND MIXING DEVICE (MIXING MEANS)

The invention claimed is:
1. A sampling method of recycled raw material, the method comprising:
a process of primarily crushing recycled raw material;
a process of separating primarily crushed raw material into three components, "scrap iron", "scrap aluminum", and "recycled raw material component other than scrap iron and scrap aluminum";
a process of performing a primary sample reduction of "the recycled raw material component other than scrap iron and scrap aluminum" which is separated at least after the primary crushing process;
a process of secondarily crushing "the recycled raw material component other than scrap iron and scrap aluminum", which is subjected to the primary sample reduction, into a size less than that in the primary crushing process and performing a secondary sample reduction of "the recycled raw material component other than scrap iron and scrap aluminum" which is secondarily crushed;
a process of obtaining a weight ratio of the three components, "scrap iron", "scrap aluminum", and "the recycled raw material component other than scrap iron and scrap aluminum" which are primarily crushed; and
a mixing process of mixing "scrap iron", "scrap aluminum", and "the recycled raw material component other than scrap iron and scrap aluminum" which is subjected to the secondary sample reduction at a mixing ratio corresponding to the weight ratio obtained in the previous process, wherein a mixture obtained in the mixing process is set as an analysis sample.

2. The sampling method of recycled raw material according to claim 1, wherein in the process of obtaining a weight ratio of the three components, "scrap iron", "scrap aluminum", and "the recycled raw material component other than scrap iron and scrap aluminum" which are primarily crushed, the weight of each of the three components, "scrap iron", "scrap aluminum", and "the recycled raw material component other than scrap iron and scrap aluminum" which are primarily crushed is measured to obtain the weight ratio.

3. The sampling method of recycled raw material according to claim 1, wherein the process of obtaining a weight ratio of the three components, "scrap iron", "scrap aluminum", and "the recycled raw material component other than scrap iron and scrap aluminum" which are primarily crushed includes a process of measuring the total weight of the recycled raw material before or after the primary crushing process, a process of measuring the weight of each of "scrap iron" and "scrap aluminum" which are separated after the primary crushing process, and a process of obtaining a weight ratio of the three components, "scrap iron", "scrap aluminum" and "the recycled raw material component other than scrap iron and scrap aluminum" based on a calculation result of the weight of "the recycled raw material component other than scrap iron and scrap aluminum", which is obtained by subtracting the weight of "scrap iron" and the weight of "scrap aluminum" from the total weight of the recycled raw material, and the measured weights of "scrap iron" and "scrap aluminum".

4. The sampling method of recycled raw material according to claim 1, wherein in the primary crushing process, the recycled raw material is crushed into a size of 20 mm or less.

5. The sampling method of recycled raw material according to claim 1, wherein in the secondary crushing process, "the recycled raw material component other than scrap iron and scrap aluminum" is crushed into a size of 5 mm or less.

6. An analysis sample of recycled raw material which is sampled using the sampling method of recycled raw material according to claim 1.

7. An evaluation method of recycled raw material, the method comprising:

a process of mixing "scrap iron", "scrap aluminum", and "the recycled raw material component other than scrap iron and scrap aluminum", which are obtained using the sampling method of recycled raw material according to claim 1, with each other to obtain an analysis sample; and a process of performing an elementary analysis of the analysis sample to measure the content of valuable metals in a certain number of samples.

8. A sampling method of recycled raw material, the method comprising:

a process of primarily crushing recycled raw material;

a process of separating primarily crushed raw material into three components, "scrap iron", "scrap aluminum", and "recycled raw material component other than scrap iron and scrap aluminum" from the primarily crushed raw material and performing primary sample reductions of the three components;

a process of secondarily crushing "the recycled raw material component other than scrap iron and scrap aluminum", which is subjected to the primary sample reduction, into a size less than that in the primary crushing process and performing a secondary sample reduction of "the recycled raw material component other than scrap iron and scrap aluminum" which is secondarily crushed;

a process of obtaining a weight ratio of the three components, "scrap iron", "scrap aluminum", and "the recycled raw material component other than scrap iron and scrap aluminum" which are primarily crushed; and a mixing process of mixing "scrap iron", "scrap aluminum" which are subjected to the primary sample reduction, and "the recycled raw material component other than scrap iron and scrap aluminum" which is subjected to the secondary sample reduction at a mixing ratio corresponding to the weight ratio obtained in the previous process, wherein a mixture obtained in the mixing process is set as an analysis sample.

9. The sampling method of recycled raw material according to claim 8, wherein in the process of obtaining a weight ratio of the three components, "scrap iron", "scrap aluminum", and "the recycled raw material component other than scrap iron and scrap aluminum" which are primarily crushed, the weight of each of the three components, "scrap iron", "scrap aluminum", and "the recycled raw material component other than scrap iron and scrap aluminum" which are primarily crushed is measured to obtain the weight ratio.

10. The sampling method of recycled raw material according to claim 8, wherein the process of obtaining a weight ratio of the three components, "scrap iron", "scrap aluminum", and "the recycled raw material component other than scrap iron and scrap aluminum" which are primarily crushed includes a process of measuring the total weight of the recycled raw material before or after the primary crushing process, a process of measuring the weight of each of "scrap iron" and "scrap aluminum" which are separated after the primary crushing process, and a process of obtaining a weight ratio of the three components, "scrap iron", "scrap aluminum" and "the recycled raw material component other than scrap iron and scrap aluminum" based on a calculation result of the weight of "the recycled raw material component other than scrap iron and scrap aluminum", which is obtained by subtracting the weight of "scrap iron" and the weight of "scrap aluminum" from the total weight of the recycled raw material, and the measured weights of "scrap iron" and "scrap aluminum".

11. The sampling method of recycled raw material according to claim 8, wherein in the primary crushing process, the recycled raw material is crushed into a size of 20 mm or less.

12. The sampling method of recycled raw material according to claim 8, wherein in the secondary crushing process, "the recycled raw material component other than scrap iron and scrap aluminum" is crushed into a size of 5 mm or less.

13. An analysis sample of recycled raw material which is sampled using the sampling method of recycled raw material according to claim 8.

14. An evaluation method of recycled raw material, the method comprising:
a process of mixing "scrap iron", "scrap aluminum", and "the recycled raw material component other than scrap iron and scrap aluminum", which are obtained using the sampling method of recycled raw material according to claim 8, with each other to obtain an analysis sample; and
a process of performing an elementary analysis of the analysis sample to measure the content of valuable metals in a certain number of samples.

15. A sampling device comprising:
a primary crusher that primarily crushes recycled raw material;
an Fe separator that separates "scrap iron" from the primarily crushed raw material;
an Al separator that separates "scrap aluminum" from the primarily crushed raw material;
recycled raw material-component-other-than-scrap-iron-and-scrap-aluminum primary sample reduction machine that performs a sample reduction of "the recycled raw material component other than scrap iron and scrap aluminum" from which "scrap iron" and "scrap aluminum" are removed by the Fe separator and the Al separator;
a secondary crusher that secondarily crushes "the recycled raw material component other than scrap iron and scrap aluminum", which is subjected to the sample reduction by the recycled-raw-material-component-other-than-scrap-iron-and-scrap-aluminum primary sample reduction machine, into a size less than that obtained by the primary crusher;
a secondary sample reduction machine that performs a secondary sample reduction of "the recycled raw material component other than scrap iron and scrap aluminum" which is secondarily crushed by the secondary crusher:,
a measuring device that measures the weights of the three components, "scrap iron", "Scrap aluminum", and "recycled raw material component other than scrap iron and Scrap aluminum" which are separated from the primarily crushed raw material; and
a mixing device that mixes "scrap iron", "scrap aluminum", and "recycled raw material component other than scrap iron and scrap aluminum" with each other at a predetermined mixing ratio set according to a measurement result of the measuring device.

16. The sampling device of recycled raw material according to claim 15, further comprising:
a scrap iron primary sample reduction machine that performs a primary sample reduction of "scrap iron" which is separated by the Fe separator; and
a scrap aluminum primary sample reduction machine that performs a primary sample reduction of "scrap aluminum" which is separated by the Al separator.

17. The sampling device of recycled raw material according to claim 15,
wherein the Fe separator is a magnetic separator, and
the Al separator is an eddy current separator.

18. A sampling device comprising:
a primary crusher that primarily crushes recycled raw material;
an Fe separator that separates "scrap iron" from the primarily crushed raw material;
an Al separator that separates "scrap aluminum" from the primarily crushed raw material;
recycled raw material-component-other-than- scrap-iron-and- scrap-aluminum primary sample reduction machine that performs a sample reduction of "recycled raw material component other than scrap-iron and scrap aluminum" from which "scrap iron" and "scrap aluminum" are removed by the Fe separator and the Al separator;
a secondary crusher that secondarily crushes "the recycled raw material component other than scrap iron and scrap aluminum", which is subjected to the sample reduction by the recycled-raw-material-component-other-than-scrap-iron-and- scrap-aluminum primary sample reduction machine, into a size less than that obtained by the primary crusher;
a secondary sample reduction machine that performs a secondary sample reduction of "the recycled raw material component other than scrap iron and scrap aluminum" which is secondarily crushed by the secondary crusher;
a measuring device that measures the total weight of the recycled raw material and the weight of each of two components including "scrap iron" and "Scrap aluminum" which are separated from the primarily crushed raw material; and
a mixing device that mixes "scrap iron", "scrap aluminum", and "the recycled raw material component other than scrap iron and Scrap aluminum" with each other at a predetermined mixing ratio set according to a measurement result of the measuring device.

19. The sampling device of recycled raw material according to claim 18, further comprising:
a scrap iron primary sample reduction machine that performs a primary sample reduction of "scrap iron" which is separated by the Fe separator; and
a scrap aluminum primary sample reduction machine that performs a primary sample reduction of "scrap aluminum" which is separated by the Al separator.

20. The sampling device of recycled raw material according to claim 18,
wherein the Fe separator is a magnetic separator, and
the Al separator is an eddy current separator.

* * * * *